United States Patent [19]

Steelman et al.

[11] 4,211,778

[45] Jul. 8, 1980

[54] USE OF CARBOTHIOLATES AS INSECTICIDES

[75] Inventors: Carrol D. Steelman, Baton Route; Doyle M. Chambers, Lake Charles, both of La.

[73] Assignee: Louisiana State University Board of Supervisors, Baton Rouge, La.

[21] Appl. No.: 942,382

[22] Filed: Sep. 14, 1978

[51] Int. Cl.$^2$ ............................................. A01N 9/00
[52] U.S. Cl. .................................................... 424/244
[58] Field of Search ................... 424/244; 260/239 BF

[56] References Cited

U.S. PATENT DOCUMENTS

| | | | |
|---|---|---|---|
| 3,198,786 | 8/1965 | Tilles et al. | 71/88 |
| 3,573,031 | 3/1971 | Tilles | 71/100 |
| 3,954,729 | 5/1976 | Sato et al. | 260/239 BF |

*Primary Examiner*—Douglas W. Robinson
*Attorney, Agent, or Firm*—Llewellyn A. Proctor

[57] ABSTRACT

An alkyl 1-hexamethyleneimine-carbothiolate in low concentration has been found insecticidally active in the treatment of substrates which contain or are susceptable to infestation by insects and their larvae, particularly Diptera, and more particularly mosquitoes. The alkyl 1-hexamethylene-carbothiolate can be formulated and applied as a solution, aerosol or admixture within which it is dispersed as an insecticidally effective ingredient.

8 Claims, No Drawings

USE OF CARBOTHIOLATES AS INSECTICIDES

In terms of the number of species, their absolute numbers and wide distribution, insects are the most eminently successful of animals. The most numerous species are the orders Coleoptera (beetles), Lepidoptera (butterflies and moths), Hymenoptera (ants, bees, wasps, etc.) and Diptera (true flies). Insects are not only annoying to man, but many carry diseases which affect man and animals, particularly domestic and game animals which are important to man.

True flies include some of the most important of all disease vectors. *Phlebotomus* sandflies transmit *Leishmania* organisms which cause oriental sore and espundia; trypanosomes causing kala azar; *Bartonella* causes Carrións disease; and viruses causing sand fly fever. *Simuliam* carry onchocerciasis; tabanid flies, and various worms including those which cause loaiasis; tsetse flies, trypanosomes of sleeping sickness; and house flies which may spread typhoid fever, dysentery and chlora. Fleas are able to transmit plaque and endemic typhus.

Among the mosquitoes (Culicidae), insects known throughout the world, *Anopheles* transmits malaria; *Aedes* transmits the viruses of dengue and yellow fever; *Culex*, and other genera, transmit the causative organism of filariasis; and are the cause of various viral illnesses including the encephalitides. The ecosystem defined as the rice growing regions of La., Calif., Ark., Miss. and Tex. produce many species and massive populations of mosquitoes. Their intensive breeding in this agroecosystem poses a menace, as well as a nuisance, not only to man but to his pastured domestic animals which they attack.

Albeit by far the majority of insects are believed to benefit man, directly or indirectly, the best known species are those considered injurious because they annoy and endanger man and animals important to man, or attack and destroy man's crops and plant products. The control of these harmful species of insects has continued to be the major objective of the applied fields of medical and veterinary entomology, and of agricultural and forest entomology, respectively.

It is, accordingly, the primary objective of the present invention to provide novel compositions, and a process for the control of population levels of insects, particularly Diptera.

A specific object is to provide novel mosquito larvacide compositions, and process useful for the control, and destruction of mosquitoes.

These and other objects are achieved in accordance with the present invention embodying novel compositions, and process for the treatment and control of insects or their larvae by contacting same, or substrates of same, with an insecticidally effective amount of said compositions. The compositions are characterized as solutions, aerosols, dispersions or powdered solids admixtures which contain an an insecticidally active ingredient a compound represented by the formula:

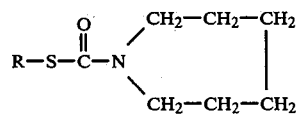

wherein R is a lower alkyl group. The process is one which comprises contacting, or applying sufficient of one or more of said compositions to insects, or their larvae or to substrates containing said insects or their larvae, especially Diptera, and more especially mosquitoes to kill a major portion of a given population of the insects.

The insecticidally active ingredient is an alkyl 1-hexamethyleneimine-carbothiolate which has heretofore been recognized as a herbicide (U.S. Pat. Nos. 3,198,786; and 3,573,031), but there appears no recognition of the value of these compounds in small concentrations as effective insecticides. Illustrative of compounds of this class are methyl 1-hexamethyleneimine-carbothiolate, ethyl 1-hexamethyleneimine-carbothiolate, n-propyl 1-hexamethyleneimine-carbothiolate, n-butyl 1-hexamethylenemine-carbothiolate, sec-butyl 1-hexamethylenemine-carbothiolate, t-butyl 1-hexamethylenemine-carbothiolate, i-propyl 1-hexamethylenemine-carbothiolate, i-butyl 1-hexamethylenemine-carbothiolate, and the like.

The alkyl 1-hexamethyleneimine-carbothiolate is applied over an area which contains the insects, e.g., mosquitoes, in concentration sufficient to kill at least about 50 percent, and preferably about 90 percent of the population of insects which are to be destroyed. It has been found that a concentration of about 2 pounds, or less, of an alkyl 1-hexamethyleneimine-carbothiolate compound, or active ingredient contained in a larger amount of applied material, is adequate to kill at least about 90 percent of the mosquito larvae and pupae spread over an acre of soil within a twenty-four hour period, and generally a concentration ranging from about 1 pound to about 2 pounds of the alkyl 1-hexamethyleneimine-carbothiolate is adequate to kill 90 percent of the mosquito larvae and pupae.

In its preferred method of application the alkyl 1-hexamethyleneimine-carbothiolate is added or injected into the water within which the mosquito larvae and pupae are contained, the alkyl 1-hexamethyleneimine-carbothiolate being added in concentration ranging from about 1 part to about 4 parts, preferably from about 2 parts to about 3 parts, per million parts by weight of water (ppm) which is generally adequate to kill 90 percent of the population of mosquito larvae and pupae within a twenty-four hour period. This method of treatment is particularly useful in the treatment of riceland agroecosystems and productive rice fields for the control of mosquito populations, which are known to be intensive mosquito breeding grounds for numerous species of mosquitoes.

It is also feasible to apply the insecticide as a powder which contains the active ingredient, or an aersol solution of the alkyl 1-hexamethyleneimine-carbothiolate can be sprayed over a geographical area, as from an aircraft, to provide the desired lethal concentration.

The following data shows the effectiveness of alkyl 1-hexamethyleneimine-carbothiolate as an insecticide when used in small concentrations for killing mosquito larvae collected from a La. rice field. The tests employed are those employed by The World Health Organization, Annexes 2A and 2B (Wld Heth Org. Techn. Rep. Ser., 170, No. 443) which were revised and combined as a result of discussions held at the WHO Expert Committee on Resistance of Vectors and Reservoirs to Pesticides which met in Geneva from 16 to 23 September 1975.

In order to demonstrate the effectiveness of alkyl 1-hexamethyleneimine-carbothiolate in low concentrations, ethyl 1-hexamethyleneimine-carbothiolate was dissolved in water and the solution employed to kill mosquitoes of the species *Culex Pipiens Quinquefasciatus*.

Sufficient mosquito larvae of the species *Culex Pipiens Quinquefasciatus* were obtained from a rice field to provide about 300 individual mosquitoes. The third or early fourth instar larvae were selected and retained initially in the water from which they were reared, those showing any abnormalities, such as a fuzzy appearance which might be indicative of parasites on the body surface were discarded. Lots of 20 to 25 of the healthy larvae were transferred, after washing to each of 24 small beakers, each containing 24 ml of water free of organic contaminants and traces of poisonous heavy metals.

Twenty-four larger glass vessels, 7.5 to 10 cm in diameter were then charged with 225 ml. of water free of organic contaminants and trace amounts of poisonous heavy metals, this providing a water depth of 2.5 to 7.5 cm and a water volume of 250 ml. To each of the vessels of water, which was maintained at a temperature of about 25° C. throughout the tests, various concentrations of ethyl 1-hexamethyleneimine-carbothiolate was added by pipetting from a stock solution. Five concentrations and an untreated control each replicated 4 times were used to determine the lethal effects of the compound. Each of the vessels were then vigorously stirred for about 30 seconds to assure complete solution of the ethyl 1-hexamethyleneimine-carbothiolate within the water. Within 15 to 30 minutes after preparation 1.0 ml of each concentration and the mosquito larvae from each of the 24 small beakers were separately added to each of the 24 larger vessels. At the end of a 24 hour period a mortality count of the moribund and dead larvae in each vessel was made, and the percentage mortalities between 10 and 90 percent for each concentration was recorded. These data were then subjected to probit analyses to determine the concentration of the ethyl 1-hexamethyleneimine-carbothiolate required to cause 50 and 90% mortality.

The data showed that 1 part of the ethyl 1-hexamethyleneimine-carbothiolate, in one million parts by weight of water, i.e., 1 ppm, was adequate to kill 50 percent of the mosquito larvae, and that 2.3 ppm of the ethyl 1-hexamethyleneimine-carbothiolate was sufficient to kill 90 percent of the larvae within the 24 hour period. These data, expressed in terms of lethal concentration (LC) for a 50 percent ($LC_{50}$) and 90 percent ($LC_{90}$) kill, provide confidence levels within the ranges 0.84–1.2 and 1.9–3.1, respectively.

In terms of the number of pounds of ethyl 1-hexamethyleneimine-carbothiolate required to treat mosquito larvae per acre to provide lethal concentrations adequate to kill 50 percent and 90 percent, respectively, of the larvae the data given in the following table is pertinent, to wit:

Table

| Lethal Concentrations Pounds/Acre In Six Inches of Water for *Culex Pipiens Quinquefasciatus* | |
|---|---|
| $LC_{50}$ | $LC_{90}$ |
| 0.74 | 1.78 |

Alkyl 1-hexamethyleneimine-carbothiolate, and ethyl 1-hexamethyleneimine-carbothiolate in particular, has also been found lethal to the larvae of mosquitoes of the species *Anopheles crucians, Anopheles quadrimaculatus, Culex erraticus,* and *Psorophora columbiae.*

Alkyl 1-hexamethyleneimine-carbothiolate has been found particularly effective in water management techniques where insecticidally effective amounts of the compound were added to the water used to flood rice fields. Various other means known to the art can also be employed in the treatment of various insect infested substrates. For example, the compound can be blended with various other materials, admixtures of solids powders, oil water emulsions within which the compound is blended, dispersions of the compound in various liquids, or solutions. Obviously, various modifications and changes can be made in the manner of application of the insecticide to various insect infested substrates, e.g., vegetation, soil, etc. without departing the spirit and scope of the present invention as will be apparent to those skilled in the art.

Having described the invention what is claimed is:

1. A process for killing insects by applying to said insects and to substrates susceptible to infestation by said insects or their larvae an insecticidally effective amount of a compound having the formula:

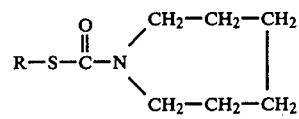

wherein R is a lower alkyl group.

2. The process of claim 1 wherein R is methyl, ethyl, n-propyl, n-butyl, sec-butyl, t-butyl, i-propyl, i-butyl.

3. The process of claim 1 wherein the compound is applied to a substrate in concentration ranging from about 1 to about 4 ppm.

4. The process of claim 3 wherein the applied concentration ranges from about 2 to about 3 ppm.

5. The process of claim 1 wherein the compound is added to water, from about 1 to about 4 ppm of the compound is dissolved in the water, and the water is applied to a soil substrate.

6. The process of claim 5 wherein the water contains from about 2 to about 3 ppm of the compound.

7. The process of claim 1 wherein the compound is admixed with soil in concentration sufficient to supply up to about 2 pounds of said compound per acre of soil.

8. The process of claim 7 wherein the compound is supplied to the soil in concentration ranging from about 1 pound to about 2 pounds.

* * * * *